United States Patent [19]
Fuisz

[11] Patent Number: 5,811,123
[45] Date of Patent: *Sep. 22, 1998

[54] METHOD OF TREATING MUCOSAL TISSUE

[75] Inventor: Richard C. Fuisz, Great Falls, Va.

[73] Assignee: Fuisz Technologies Ltd., Chantilly, Va.

[ * ] Notice: The term of this patent shall not extend beyond the expiration date of Pat. No. 5,622,717.

[21] Appl. No.: 465,974

[22] Filed: Jun. 6, 1995

Related U.S. Application Data

[60] Division of Ser. No. 113,485, Aug. 27, 1993, Pat. No. 5,651,987, which is a continuation-in-part of Ser. No. 081,336, Jun. 14, 1994, Pat. No. 5,622,717, which is a continuation-in-part of Ser. No. 808,599, Dec. 17, 1991, abandoned.

[51] Int. Cl.⁶ .......................... A61K 9/10; A61K 9/14
[52] U.S. Cl. ........................... 424/488; 514/925
[58] Field of Search ............... 424/484, 485, 424/487, 488, 500, 501; 514/925

[56] References Cited

U.S. PATENT DOCUMENTS

| | | | |
|---|---|---|---|
| Re. 32,016 | 10/1985 | Esders et al. | 435/28 |
| 796,528 | 8/1905 | Pollock | 425/9 |
| 816,055 | 3/1906 | Zoeller | 425/9 |
| 847,366 | 3/1907 | Pollock | 425/9 |
| 856,424 | 6/1907 | Robinson | 425/9 |
| 1,489,342 | 4/1924 | Brent | 425/9 |
| 1,541,378 | 6/1925 | Parcell | 425/9 |
| 3,118,396 | 1/1964 | Brown et al. | 107/8 |
| 3,118,397 | 1/1964 | Brown et al. | 107/8 |
| 3,125,967 | 3/1964 | Bowe | 107/8 |
| 3,523,889 | 8/1970 | Eis | 210/20 |
| 3,557,718 | 1/1971 | Chivers | 426/658 |
| 3,686,000 | 8/1972 | Lawrence | 99/134 |
| 3,749,671 | 7/1973 | Gedge et al. | 252/89 |
| 3,981,739 | 9/1976 | Dmitrovsky et al. | 127/60 |
| 3,991,766 | 11/1976 | Schmitt et al. | 128/335.5 |
| 4,004,039 | 1/1977 | Shoaf et al. | |
| 4,056,364 | 11/1977 | Dmitrovsky et al. | 23/273 |
| 4,072,658 | 2/1978 | Okamoto et al. | 260/49 |
| 4,086,418 | 4/1978 | Turbak et al. | 536/30 |
| 4,159,210 | 6/1979 | Chen et al. | 127/29 |
| 4,164,448 | 8/1979 | Röeschlau et al. | 435/11 |
| 4,166,005 | 8/1979 | Masurekar et al. | 436/190 |
| 4,168,205 | 9/1979 | Danninger et al. | 435/10 |
| 4,178,393 | 12/1979 | Gregersen | 426/653 |
| 4,186,251 | 1/1980 | Tarbutton | 435/11 |
| 4,194,063 | 3/1980 | Frank et al. | 435/12 |
| 4,199,373 | 4/1980 | Dwivedi et al. | 127/60 |
| 4,241,178 | 12/1980 | Esders et al. | 435/15 |
| 4,271,199 | 6/1981 | Cherukuri et al. | 426/5 |
| 4,293,292 | 10/1981 | Israel | 425/9 |
| 4,335,232 | 6/1982 | Irwin | 528/128 |
| 4,338,350 | 7/1982 | Chen et al. | 426/658 |
| 4,362,757 | 12/1982 | Chen et al. | 426/599 |
| 4,382,963 | 5/1983 | Klose et al. | 426/3 |
| 4,382,967 | 5/1983 | Koshida | 426/96 |
| 4,501,538 | 2/1985 | Bray | 425/9 |
| 4,504,509 | 3/1985 | Bell et al. | |
| 4,581,234 | 4/1986 | Cherukuri et al. | 426/3 |
| 4,684,534 | 8/1987 | Valentine | 427/3 |
| 4,722,845 | 2/1988 | Cherukuri et al. | 426/5 |
| 4,747,881 | 5/1988 | Shaw et al. | 106/209 |
| 4,765,991 | 8/1988 | Cherukuri et al. | 426/3 |
| 4,797,288 | 1/1989 | Sharma et al. | 424/476 |
| 4,816,283 | 3/1989 | Wade et al. | 426/565 |

(List continued on next page.)

FOREIGN PATENT DOCUMENTS

| | | |
|---|---|---|
| 489211 | 7/1986 | Switzerland . |
| 2 155 934 | 3/1985 | United Kingdom . |
| WO 85/03414 | 1/1985 | WIPO . |
| WO 91/18613 | 5/1991 | WIPO . |

*Primary Examiner*—Edward J. Webman
*Attorney, Agent, or Firm*—Sandra M. Nolan; Richard D. Schmidt

[57] ABSTRACT

Anti-ulcer compositions are disclosed having therapeutic agents dispersed in a soluble matrix formed by melt spinning the therapeutic agent with a carrier and hydrogel. Methods of treating mucosal ulcer-bearing tissue and preparing the matrix are also disclosed. One embodiment includes use of gastric irritating bio-affecting agents in which case the composition is preventative as well as therapeutic.

16 Claims, 4 Drawing Sheets

U.S. PATENT DOCUMENTS

| | | | |
|---|---|---|---|
| 4,839,184 | 6/1989 | Cherukuri et al. | 426/307 |
| 4,846,643 | 7/1989 | Yamamoto et al. | 425/7 |
| 4,853,243 | 8/1989 | Kahn et al. | 426/564 |
| 4,855,326 | 8/1989 | Fuisz | 514/777 |
| 4,867,986 | 9/1989 | Desai et al. | 424/464 |
| 4,871,501 | 10/1989 | Sugimoto et al. | 264/211.22 |
| 4,872,821 | 10/1989 | Weiss | 425/9 |
| 4,882,144 | 11/1989 | Hegasy | 424/80 |
| 4,885,281 | 12/1989 | Hanstein et al. | 514/53 |
| 4,900,563 | 2/1990 | Cherukuri et al. | 426/5 |
| 4,931,293 | 6/1990 | Cherukuri et al. | 426/5 |
| 4,933,192 | 6/1990 | Darling | 426/98 |
| 4,939,063 | 7/1990 | Tamagawa | 430/138 |
| 4,981,698 | 1/1991 | Cherukuri et al. | 426/5 |
| 4,988,529 | 1/1991 | Nakaya et al. | 426/569 |
| 5,009,893 | 4/1991 | Cherukuri et al. | 424/440 |
| 5,009,900 | 4/1991 | Levine et al. | 426/96 |
| 5,037,662 | 8/1991 | Poulose et al. | 426/52 |
| 5,039,446 | 8/1991 | Estell | 252/174.12 |
| 5,041,377 | 8/1991 | Becker et al. | 435/220 |
| 5,057,328 | 10/1991 | Cherukuri et al. | 426/5 |
| 5,066,218 | 11/1991 | Silver | 426/20 |
| 5,073,387 | 12/1991 | Whistler | 426/7 |
| 5,077,076 | 12/1991 | Gonsalves et al. | 426/565 |
| 5,079,027 | 1/1992 | Wong et al. | 426/633 |
| 5,104,674 | 4/1992 | Chen et al. | 426/573 |
| 5,110,614 | 5/1992 | Corbin et al. | 426/555 |
| 5,164,210 | 11/1992 | Campbell et al. | 426/5 |
| 5,169,657 | 12/1992 | Yatka et al. | 426/5 |
| 5,169,658 | 12/1992 | Yatka et al. | 426/5 |
| 5,171,589 | 12/1992 | Richey et al. | 426/5 |
| 5,173,317 | 12/1992 | Hartman et al. | 426/6 |
| 5,173,322 | 12/1992 | Melachouris et al. | 426/580 |
| 5,175,009 | 12/1992 | Synosky et al. | 426/3 |
| 5,196,199 | 3/1993 | Fuisz | 424/401 |
| 5,236,734 | 8/1993 | Fuisz | 426/641 |
| 5,238,696 | 8/1993 | Fuisz | 426/641 |

METHOD OF TREATING MUCOSAL TISSUE

This is a divisional application of U.S. Ser. No. 08/113,485 filed Aug. 27, 1993, now U.S. Pat. No. 5,651,987, which is a continuation-in-part of U.S. Ser. No. 08/081,336 filed Jun. 14, 1994, now U.S. Pat. No. 5,642,717; which is a continuation-in-part of U.S. Ser. No. 07/808,599 filed Dec. 17, 1991, abandoned.

BACKGROUND OF THE INVENTION

The present invention relates to ulcer treatments. In particular, the present invention relates to the use of dosage forms containing anti-ulcer agents dispersed in a soluble matrix.

Sucralfate is a therapeutic compound useful for treatment of various gastrointestinal disorders. Sucralfate accelerates the healing of gastric and duodenal ulcers and also finds use as a symptomatic treatment for disturbances such as dyspepsia and reflux.

Sucralfate displays its action in the acid medium of the digestive tract where it lines ulcerated mucous membranes of the stomach and duodenum with a protective coating. The preferential binding affinity of sucralfate for ulcerated areas of mucous membrane results in increased protection and accelerated healing of ulcers as well as regeneration of the mucous membrane.

Although sucralfate is usually taken orally in the form of tablets, other dosage forms are known. For example, U.S. Pat. No. 4,885,281 discloses an aqueous suspension containing sucralfate, xanthum gum and a "peptiser". Peptisers such as salts of inorganic or organic acids are added to ensure that the xanthan gum does not separate out of the suspension by gel formation.

Belgium Patent No. 900,605 discloses a composition of sucralfate and a nonsteroidal anti-inflammatory product. The compositions were prepared for administering to mammalian test specimens by suspending the active substances in an aqueous medium containing 0.5% sodium CMC (carboxymethylcellulose).

The preparation of melt-spun medicament-containing products is known. For example, commonly-assigned U.S. Pat. No. 4,855,326, which is incorporated by reference herein, discloses combining a medicament with a melt-spinnable carrier agent, preferably a mixture of sucrose and lactose, and then melt-spinning the mixture to form a spun product.

Similarly, commonly-assigned U.S. Pat. No. 4,997,856, also incorporated by reference herein, discloses melt spun, compacted dispersible systems containing a medicament, saccharide and an oleaginous substance such as a food oil.

In keeping with the foregoing, improvements are continuously being sought using high shear and/or heat processing to enhance the delivery of medicaments. In the case of anti-ulcer medicaments such as sucralfate, an investigation is being conducted to improve the protective and therapeutic action of the medicament on ulcerated areas of mucous membranes.

It is an object of the present invention to provide an improved method of treatment using medicaments spun in a matrix carrier.

It is a further object of the present invention to provide improved methods and compositions for preventing and treating ulcerated mucosa.

Other and further objects will become apparent to the artisan in view of the present disclosure, and the scope of the present application is not to be limited by the objects set forth above.

BRIEF DECRIPTION OF THE DRAWINGS

FIG. 1 is a photograph of two containers of sucralfate compositions, using HPMC as a thickener, which were reconstituted with water and shaken to obtain a suspension. The container marked "Processed-Shaken" is a flash flow formed matrix made in accordance with the present invention. The container marked "Unprocessed-Shaken" shows a suspension of the identical formulation which has not been flash flow processed, but mixed as a simple powdered mixture. The wettability, uniformity and completeness of the resultant dispersion is evident from the photograph.

FIG. 2 is a photograph of two containers of sulcrafate compositions, using HPMC as a hydrogel, which were reconstituted with water without shaking. The "Processed-Unshaken" and "Unprocessed-Unshaken" markings have the meanings as in FIG. 1. The failure of the unprocessed simple mixture to fully wet and fall into suspension is evident.

FIG. 3 is a photograph of two containers of sucralfate compositions using xanthan gum as a hydrogel suspension aid and which were constituted with water and shaken to obtain a suspension. The "Processed-Shaken" and "Unprocessed-Shaken" markings have the meanings as in FIG. 1. The wettability, uniformity and completeness of the resultant dispersion formed from the inventive (Processed) matrix compositions. The failure of the unprocessed mixture to fully wet and form a uniform suspension is evident.

FIG. 4 is a photograph of two containers of sucralfate compositions using xanthan gum as a hydrogel suspension aid and which were reconstituted with water without shaking. The failure of the unprocessed mixture, as compared to the inventive flash flow processed composition; to fully wet and fall into suspension is evident.

SUMMARY OF THE INVENTION

The present invention includes anti-ulcer compositions formed by having a medicament dispersed in a soluble matrix. The soluble matrix is formed by subjecting the feedstock to physical and/or chemical changes associated with flash flow processing, such as by melt-spinning the medicament with a mixture of a carrier material and a hydrogel. The anti-ulcer compositions can either be placed directly on the ulcer-bearing tissue/mucosa or may be dispersed in a liquid before contacting the affected tissue.

The medicament included in the composition of the present invention is preferably sucralfate. Alternatively, $H_2$-blocking agents such as cimetidine and the like or omeprazole may also be included.

The carrier materials included in the mixture are a saccharide-based and preferably materials such as maltodextrin, maltooligosaccharides or polydextrose. The hydrogel is selected from materials such as xanthan gum, guar gum and carrageenan. In a preferred embodiment, the melt spinning mixture also includes an oleaginous substance such as a vegetable oil. A method of preparing such anti-ulcer compositions is also disclosed.

The composition of the present invention can also include an analgesic and non-steroidal anti-inflammatory (NSAI) agent. The non-steroidal anti-inflammatory agent may be selected from the various classes of such compounds, e.g., salicylates, acetic acids, propionic acids, fenamates, oxicams, and oxidoles. A processing aid, such as glycerin, can be used in manufacture of the composition.

The composition of the present invention can also include steroids or other gastric irritating drugs. The steroids may be andrenocorticoids such as betamethasone, cortisone, dexamethasone, hydrocortisone, methylprednisolone, paramethasone, prednisolone, prednisone, triamcinolone or corticotropins and the like. Examples of steroids in clude, but are not limited to, medicaments set forth by trade name as follows: Aristocort - Lederle; Hydrocortone - Merck Sharp & Dohme; Kenalog (in Orabase) - Squibb; Cortone - Merck Sharp & Dohme; Decadron - Merck Sharp & Dohme; and Medrol - Upjohn.

In yet another embodiment an antacid can be included in the composition. The antacid can be incorporated in the feedstock before being processed under flash-flow conditions, or, alternatively, it can be separately processed under flash-flow condition and combined in a delivery system. For example, the antacid can be processed separately to form flakes which can then be combined with flakes bearing an anti-ulcer medicament and optionally an analgesic, by tabletting the flakes together in a single tablet.

The present invention also includes a method of treating ulcer-bearing tissue. The method includes contacting the affected tissue with an anti-ulcer medicament dispersed in a soluble matrix as set forth above. Preferably, the medicament-contain ing matrix has been dispersed in a liquid such as water before contacting the ulcer-bearing tissue.

In a further embodiment, the present invention includes a pharmaceutical composition having rapid delivery and enhanced adherence to mucosal tissue. The pharmaceutical composition comprises a solid matrix having suspended therein a medicament, the matrix being formed by flash-flow melt-spinning a mixture of: a melt-spinnable carrier material present in an amount sufficient to form a flash-flow melt-spun matrix when the medicament is dispersed therein; a medicament present in an amount sufficient to achieve a therapeutic effect; and a hydrogel which demonstrates mucosal adherence properties and which is present in an amount sufficient to assist in suspending the medicament in the matrix. The medicament can be any drug which acts systematically. For example, it may be selected from the group consisting of anti-infectives and anti-lipid agents. The carrier can be selected from the group consisting of maltodextrins, corn syrup solids, polydextroses, maltooligosaccharides and mixtures thereof. The hydrogel can be selected from a number of water-soluble polymers, hydrocolloids or hydrophilic polymers which are useful as mucosal adherence materials, such as xanthan gum, guar gum, carrageenan gum, gum tragacanth, sodium alginate, gum karaya, locus bean gum, gum acacia and mixtures thereof. The hydrogel is present in an amount from about 0.2 to about 5.2% by weight of the matrix. The solid matrix may further contain an oleaginous substance, which, for example, may be selected from the group consisting of corn oil, sunflower oil, olive oil, vegetable oils and mixtures thereof. Further, the hydrogel may be a cellulose. A non-limiting list of cellulose hydrogels useful in the present invention include those selected from the group consisting of hydroxypropylmethylcellulose, hydroxyethylcellulose, methylcellulose, carboxymethylcellulose, hydroxymethylcellulose and mixtures thereof.

As a result of the present invention, anti-ulcer compositions are provided which present therapeutic agents in a rapidly soluble form. In addition, since the therapeutic agents are melt spun with a hydrogel in addition to a soluble carrier, the composition demonstrates mucosal adherence properties and enhanced mouthfeel due to the thickening effect of the hydrogel. These added features provide an enhanced therapeutic effect as well by rapidly placing the anti-ulcer medicament in contact with the affected tissue and affixing it there for a period of time. The hydrogel also acts to assist in suspending the medicament during melt spinning within the spun matrix. The hydrogel is present in an amount sufficient to assist in suspending the medicament in the matrix.

Moreover, when the active agents set forth above are prepared in accordance with the present invention, the product has a markedly enhanced tabletting capability. This product is ideal for preparing tabletted delivery systems such as pills, etc.

Yet another advantage is that the compositions of the present invention provide good coating action for internal tissue surfaces of the body by virtue of their substantially uniform adherence to mucosal tissue.

For a better understanding of the present invention, reference is made to the following description, and its scope will be pointed out in the appended claims.

DETAILED DESCRIPTION OF THE INVENTION

Figure 1:

The anti-ulcer compositions of the present invention are formed by melt spinning medicaments with a mixture of a carrier material and hydrogel so that the medicament is suspended in a soluble matrix.

When a non-steroidal anti-inflammatory agent is included, sucralfate and the NSAI agents are admixed prior to processing. In a preferred embodiment, the carrier material is also mixed with the active ingredients prior to processing. A processing aid can be used to provide bulk for thorough mixing. Glycerin is useful as a processing aid.

The active ingredients are subjected to flash-flow processing. Flash-flow processing can be accomplished several ways. Flash heat and flash shear are two such processes which can be used. In the flash heat process, the feedstock material is heated sufficiently to create an internal flow condition which permits part of the feedstock to move at a subparticle level with respect to the rest of the mass and exit openings provided in the perimeter of a spinning head. The centrifugal force created in the spinning head flings the flowing feedstock material outwardly from the head so that it reforms with a changed structure. The force required to separate and discharge a flowable feedstock is centrifugal force which results from the spinning head. The flash heat process is one process for producing the product of this invention.

In the flash shear process, a shearform matrix is formed by raising the temperature of the feedstock material which includes a nonsolublized-carrier to a point where the carrier such as a saccharide-based material undergoes internal flow upon application of a fluid shear force. The feedstock is advanced and ejected while in internal flow condition, and subjected to disruptive fluid shear forces to form multiple parts or masses which have morphology different from that of the original feedstock.

The multiple masses are cooled substantially immediately after contact with the fluid shear force and are permitted to continue in a free-flow condition until solidified.

In the flash heat process, a spinning process is used herein, wherein the medicament is combined with a carrier and is spun with "cotton candy" fabricating type equipment. The floss spinning machine used herein can be any cotton candy type machine, such as the Econofloss Model 3017 manufactured by Gold Metal Products Company of Cincinnati, Ohio. It will be appreciated by those skilled in the art from the present description that any apparatus or physical process which provides similar forces and temperature gradient conditions can also be used. For simplicity in disclosing and describing this invention, the term "melt-spinning" will be understood to mean a process which includes a combination of temperature, shear, flow, flow rate, mechanical forces and thermal gradients of the type utilized in a cotton candy type machine.

In melt-spinning, the stock material, historically sucrose, is melted and forced through spinerettes. Conventional equipment includes a rotating spinning head surrounded by a bowl into which the fibers are spun. Typically, the temperature of the grid in the spinning machine required for spinning sucrose is from about 180° F. to about 266° F. at operating speeds of about 3800 RPM. Other saccharides such as maltodextrins and polydextrose, however, can be spun at temperatures as much as 30 to 40% lower and thus permit many heat-sensitive materials to safely undergo melt spinning. It has also been discovered that the extremely short amount of time the medicaments, saccharides and hydrogels are exposed to the melt spinning temperature and shear allows the inventive matrix to be formed without harm.

The flash shear process can be carried out in an apparatus which has means for increasing the temperature of a non-solubilized feedstock and means for simultaneously advancing it for ejection. A multiple heating zone twin screw extruder can be used for increasing the temperature and advancing feedstock. The second element of the apparatus is a means for ejecting the feedstock in a condition for shearing it to provide the product. The means for ejecting is in fluid communication with the means for increasing the temperature and is arranged at the point to receive the feedstock while it is in the internal flow conditions. The means for ejecting the feedstock is preferably a nozzle which provides high pressure ejection of the feedstock material. For a description of various apparati which can be used to produce the inventive delivery systems, see copending U.S. Ser. No. 07/965,504, filed Oct. 23, 1992 entitled "Process for Making Shearform Matrix", which is herein incorporated by reference.

Various anti-ulcer agents, such as $H_2$-blocking agents may be included in the anti-ulcer composition of the present invention. A non-limiting list of such agents include cimetidine, ranitidine, nizatidine and famotidine. Alternatively, anti-ulcer agents such as omeprazole may be selected. In a preferred embodiment, however, the anti-ulcer agent is sucralfate. Mixtures of the above-identified medicaments are also contemplated.

The anti-ulcer agent will be present in amounts up to 50% by weight and preferably from 0.1 to about 20% by weight of the matrix. Most preferably, however, the medicament is present in amounts of from about 0.5 to about 15% by weight of the matrix. The amount of medicament in the matrix is that amount sufficient to achieve the desired therapeutic result. The optimum dosing of the anti-ulcer medicaments is left with the skill of the artisan.

The anti-ulcer medicament is melt spun with a mixture of a carrier material and hydrogel. The carrier material is preferably a saccharide-based material. A non-limiting list of suitable saccharides include sucrose, maltose, fructose, glucose and lactose. Alternatively, carrier materials can be selected from maltodextrins, polydextrose, corn syrup solids, maltooligosaccharides and mixtures thereof.

The hydrogels included in the melt-spinning mixture are selected from materials such as xanthan gum, guar gum, carrageenan gum, gum tragacanth, similar materials, and mixtures thereof. The hydrogel will be present in an amount of from about 0.2% to about 4% by weight of the matrix, with amounts of from about 0.8 to about 2.5% being preferred.

Hydrogels, which may also be referred to as water-soluble polymers, hydrocolloids or hydrophilic polymers, demonstrate the property of being able to adhere to mucous membranes. Materials such as pectins, gelatin, celluloses and polycarbophil are also of use. By including such mucous-adhering materials in the matrix, the anti-ulcer medicament can be maintained in contact with the affected area, that is, ulcer-bearing tissue. For example, upon contact with ulcer-bearing mucosal tissue, the saccharide portion of the matrix quickly dissolves, leaving the medicament and hydrogel adhering to the affected area. Even when the matrix is dispersed in a liquid before administration, adherence of the medicament to mucosal areas is observable. Thus, the therapeutic properties of the medicament can be directed and affixed to the particular area needed.

Nonlimiting examples of cellulose hydrogels which are useful in the present invention include hydroxypropylmethylcellulose (HPMC), hydroxyethylcellulose(HEC), methylcellulose, carboxymethyl-cellulose(CMC), hydroxymethylcellulose(HMC) and mixtures thereof. As previously mentioned, the matrices of the present invention can be used to rapidly form suspensions. The ability to form suspensions is greatly enhanced over conventional simple mixtures and processing techniques. This enhancement is related to the unique morphology of the solid formed matrix which provides greater surface area contact between the soluble carrier material and the reconstituting medium, e.g. water.

Unprocessed mixtures, i.e., mixtures of medicament, carrier and hydrogel which have not been melt spun produce only partially wettable suspensions, which are therefore less uniform, less complete and consequently less effective at deliverying the drug.

A variety of medicaments in addition may be added to sucralfate to the compositions of the present invention. For the purpose of this invention, medicaments shall include drugs and other bioeffecting agents. Other useful drugs include, without limitation, those disclosed in U.S. Pat. No. 4,855,326 to Fuisz, which is incorporated herein by reference. Examples of classifications of these medicaments include acne preparations, analgesics, antipyretics, antacids, antiflatulents, anthelmintics, antianginals, antianxietals, antiarrythymics, antiarthritics, anticoagulants, antithrombolics, anticonvulsants, antiparkinson agents, antidepressants, antidiarrheals, antifungals, antitrichomonals, antivirals, antigout agents, antihistamines, antipruritics, antihypertensives, anti-infectives, antimigranes, antinauseants (antiemedics), antineoplastics, antiulcer agents, antireflux agents, antispasmodics, bronchial dialaters, anti-asthmatics, cardiac agents, contraceptives, hormonals, steroids, cough/cold remedies, diuretics, hypoglycemics, hypolipidemics, laxatives, tranquilizers, muscle relaxants, opthalmic preparations, mineral supplements, sedatives, hypnotics, vitamins and mixtures thereof. Preparations using these medicaments for their intended purposes can take a variety of forms including tablets, lozenges, granules or powders, capsules, elixirs, creams, solutions, syrups as well as other forms or delivery vehicles.

The suspensions formed by the present invention can be tested using a shake test, whereby the solid matrices are reconstituted with liquid medium, i.e. water, shaken and the resultant dispersion observed for uniformity, completeness and stability. As would be expected, wettability of the matrix is extremely important in creating a proper dispersion. Wettability is the ability of a solid to make its surface available to the reconstituting liquid, with little or no clumping or caking, and rapidly dissolve or disperse. Uniformity of suspension refers to the ability of the composition to completely and uniformly disperse in the reconsituting medium. Stability refers to the ability of the particles to remain in suspension for extended periods of time, as well as the ability to be resuspended by a shaking motion, without irreversibly clumping or agglomerating during the settling out process.

In the preferred embodiment of the present invention, whereby the carrier, medicament and hydrogel are melt-spun together to form the resultant matrices, wettability is particularly enhanced and dispersions made from these matrices have excellent speed of formation, uniformity and completeness, as well as stability. The medicaments are present in amounts useful for the intended purpose, which can be determined by routine experimentation by those skilled in the art.

In a further embodiment of the present invention, the mixture of the carrier material and hydrogel can also include an oleaginous substance which functions to assure that as the matrix is formed during melt spinning, the active ingredient is substantially evenly distributed in the carrier. In this regard, oleaginous substances such as polyvinylpyrrolidone (PVP) or vegetable oils such as corn oil, sunflower oil, olive oil and mixtures thereof may be present in amounts of from about 2 to about 20% by weight of the matrix, with amounts of from about 5 to about 15% being preferred.

The medicament, hydrogel, and carrier material may be combined prior to or during melt spinning. For example, the mixture containing the carrier and hydrogel are first combined into a uniform mixture before adding the medicament and any optionally present materials such as flavors, sweeteners or oleaginous materials.

In one embodiment, the composition can also include a non-steroidal anti-inflammatory (NSAI) agent selected from the various classes of such compounds. Such classes include, for example, salicylates such as acetylsalicylic acid and diflunisal; acetic acids such as indomethacin, sulindac, tolmetin, diclofenac, and etodolac; propionic acids such as flurbiprofen, indoprofen, naproxen, and ketoprofen; fenamates such as meclofenamate; oxicams such as piroxicam; and oxindoles such as tenidap.

When the composition incudes an NSAI agent, the actives are preferably mixed prior to flash-flow processing. The actives can be mixed with a processing aid which can be glycerin, for example.

The anti-ulcer composition may also optionally include a flavorant. Flavorants include flavors, sweeteners and combinations thereof. The flavors may be natural, artificial or mixtures thereof while the sweeteners may be natural, artificial or high intensity sweeteners or mixtures thereof. Such flavorant materials can be melt spun with the medicament and carrier/hydrogel mixture so that the flavorant is also dispersed within the spun matrix. The amount of flavorant included in the matrix will be a matter of preference for the artisan. It is anticipated that the flavorant will be present in amounts of from about 0.01 to about 3% by weight of the matrix. In addition, the anti-ulcer compositions prepared in accordance with the present invention may also include materials such as colorants, anti-oxidants, preservatives, and the like.

Depending upon the carrier marerial selected for inclusion in the matrix, the melt-spun medicament product will be in the form of floss, flakes, spicules and the like. In any event, the scope of the present invention is not confined to the physical form of the product, so long as the medicament is sufficiently dispersed throughout.

In an alternative embodiment, antacid can also be included. Antacids are any alkaline substance which can be taken internally to neutralize stomach acidity. Substances which can be used as antacid include aluminum hydroxide, calcium carbonate, magnesia and alumina oral suspensions, magnesium oxide, magnesium trisilicate, magaldrate, simethicone, and sodium bicarbonate. Other substances can be used and the scope of the invention is not limited to those substances set forth above.

The embodiment which includes antacids can be prepared with the antacid combined in the feedstock with the anti-ulcer medicament and/or analgesic before flash-flow processing. However, in yet another alterative, antacid can be flash-flow processed separately and then combined in a delivery system such as a tablet, capsule, powder, etc. For example, when the flash-flow product is a flake, separate anti-ulcer flakes and antacid flakes can be mixed and then tabletted. The resulting tablet carries both actives intimately bound together in a delivery system, yet physically separated to reduce chemical interaction. The practitioner will realize yet other methods for providing the antacid with the anti-ulcer medicament and, optionally, analgesic compounds using the flash-flow process, and it is intended to include these other methods which are within the scope of the present invention.

If desired, the resultant medicament-containing spun matrix can be compacted to less than 15% of the as spun volume. An example of such compacting methods is set forth in commonly- assigned U.S. Pat. No. 4,997,856, the disclosure of which is incorporated herein. In addition, the spun matrix may also be reduced in particle size such as by milling to provide medicament containing either "particles" or "particulate".

A further aspect of the present invention is a method of treating ulcer-bearing tissue. The method includes contacting ulcer-bearing tissue with an anti-ulcer medicament dispersed in a soluble matrix formed by melt-spinning the medicament with a mixture of a carrier material and a hydrogel, such as that set forth above as the anti-ulcer composition.

The medicament containing matrix may be placed in contact with the ulcer-bearing tissue in the as-spun form, as a compacted wafer or after being dispersed in a liquid. In the situations where the matrix is affixed directly to ulcer-bearing tissue, the presence of the hydrogel in the matrix allows the medicament to be affixed at the site of treatment. Alternatively, an effective amount of anti-ulcer composition can be dispersed water and, after dissolving, can be taken orally for treatment of mouth or other gastrointestinal mucous-bearing tissue ulcers. The dosages can be varied depending upon the requirements of the patient and the severity of the condition being treated. The actual optimum dosage is within the skill of the artisan.

The compositions of the present invention may also be used as antacid substitutes for palliative relief of dyspepsia, reflux, gastritis and the like. In short, it is anticipated that the medicament-containing spun matrix can be used for any therapeutic indication for which the medicament included in the matrix is suited. Moreover, when the compositions of the present invention include NSAI agents, the unique combination is also preventative in nature.

EXAMPLES

The following examples serve to provide further appreciation of the invention but are not meant in any way to restrict the effective scope of the invention. Unless indicated otherwise, the Econofloss machine referred to above was used to form the flash-flow product.

EXAMPLE 1

ANTI-ULCER COMPOSITION

| INGREDIENTS | WT. (GRAMS) |
| --- | --- |
| Sucralfate (Powder) | 25.0 |
| Xanthan Gum | 2.0 |
| Corn Oil | 12.5 |
| Peppermint Oil | 0.5 |
| Maltodextrin 35R (Corn Syrup Solid) | 209.5 |

In this example, a sucralfate-containing anti-ulcer composition was prepared. Initially, the carrier material was prepared by mixing the xanthan gum and maltodextrin until a substantially homogeneous mixture was obtained. Thereafter, the sucralfate, corn oil and peppermint oil flavorant were added while mixing was continued. The resultant mixture was then spun at a low setting. A white spicule-like flake was obtained.

A one tablespoon quantity of the resulting matrix was added to a glass of tap water at room temperature. After quickly dissolving, a colloidal suspension was formed which had a viscosity thicker than tap water.

The resultant mixture was ingested by a host having distress from an ulcerated stomach. The inventive composition provided dramatic relief of stomach ulcer pain instantaneously. It appears that the unique combination of ingredients subjected to the high shear and heat processing had a remarkable effect on the speed and the extent of the treatment.

In the case of treatment of mouth ulcers, one tablespoon of the resulting matrix is added to two tablespoons of tap water to obtain a viscous solution which has excellent coating properties. The viscous solution provides excellent immediate and sustained relief when used for oral cavity ulcers.

EXAMPLE 2

ANTI-ULCER COMPOSITION

| INGREDIENTS | WT. (GRAMS) |
| --- | --- |
| Sucralfate (Powder) | 25.0 |
| Xanthan Gum | 1.68 |
| Glycerin | 11.25 |
| Maltodextrin 35R (Corn Syrup Solid) | 212.07 |

In this example, a sucralfate-containing anti-ulcer composition was prepared. Initially, the carrier material was prepared by mixing the xanthan gum, sucralfate and glycerin until a substantillay homogeneous mixture was obtained. Thereafter, the Maltodextrin was added while mixing was continued. The resulting mixture was then spun at a low setting. A white spicule-like flake was obtained.

Three tablespoons of the spun matrix was mixed with six tablespoons of water to make a viscous liquid mixture. The viscous mixture was used as a mouth rinse by a host having severe mouth ulcerations. About one day after using the viscous rinse, the host observed substantially reduced irritaiton of the ulcerated areas, especially when eating food.

EXAMPLE 3

ANTI-ULCER COMPOSITION

| INGREDIENTS | WT. (GRAMS) |
| --- | --- |
| Cimetidine (Powder) | 5.0 |
| Xanthan Gum | 2.0 |
| Corn Oil | 12.5 |
| Peppermint Oil | 0.5 |
| Maltodextrin 35R (Corn Syrup Solid) | 209.5 |

In this example, the process set forth in Example 1 is repeated except that the anti-ulcer agent cimetidine is used. A tablespoon quantity of the resultant spun matrix is added to a glass of water and quickly dissolves forming a somewhat viscous colloidal suspension.

The suspension is ingested by a host suffering gastric distress. The medication quickly relieves the stomach pain associated with gastritis and dyspepsia. The viscous suspension is also effective in relieving the discomfort associated with gastrointestinal reflux, since the viscous liquid adheres to the upper portion of the gastric mucosa as well as stomach contents.

EXAMPLE 4

ANTI-ULCER COMPOSITION

| INGREDIENTS | WT. (GRAMS) |
| --- | --- |
| Sucralfate (Powder) | 25 |
| Xanthan Gum | 2 |
| Olive Oil | 12.5 |
| Spearmint Oil | 0.5 |
| Maltodextrin 35R (Corn Syrup Solid) | 209.5 |

In this example, the medicament-containing matrix is prepared as in the Example 1, except that after the matrix is formed, it is compacted to about 15% of its as-spun volume in the form of wafers.

The wafers were then placed on ulcer-bearing oral cavity tissue of an affected host without being dissolved in water. Once placed on the ulcer-bearing tissue, the saccharide portion of the matrix quickly dissolves and the hydrogel portion of the composition, xanthan gum, along with the medicament remain affixed to the oral cavity ulcer-bearing tissue to provide instantaneous relief from the discomfort associated with the ulcerated tissue in the oral cavity.

EXAMPLE 5

In this example, the anti-ulcer medicament sucralfate was mixed with the NSAI agent acetylsalicylic acid. Glycerin was used as a processing aid and the active ingredients mixed by mortar and pestle. Corn syrup solids (D.E.=36.5), Maltrin-365, was added and mixed well. Xanthan gum was also added to form the feedstock. The ingredients were mixed in the amounts set forth in the Table below.

| NSAI PLUS SUCRALFATE/HYDROGEL | | | |
|---|---|---|---|
| Active wt % | CSS DE = 36.5 wt % | Aid wt % | Hydrogel wt % |
| Sucralfate 10% Acetylsalicylic acid 10% | Maltrin-365 74% | Glycerin 5% | Xanthan Gum 1% |

The feedstock was processed by subjecting the feedstock to flash-flow conditions in a Tornado spinning machine which had been modified to control two parameters: temperature of the heating element, and speed (RPM) of the rotating head. The diameter of the head was 5.5 inches. The feedstock was processed at 3600 RPM and at 135° C.

The resulting product was in the form of flakes which contained a substantially uniform dispersion of the active ingredients. Furthermore, the product had a consistent color and texture, which made it easily adaptable for inclusion in a delivery system such as a tablet.

The above example can also be prepared with ibuprofen as a NSAI agent. The results are a flake which can be easily used in the formation of a delivery means such as a tabletted pill or capsule.

EXAMPLES 6 & 7

Corn Syrup Solids (D.E.=36.5) were melt spun in combination with three drugs to produce a flake-like matrix useful in the present invention. Two examples of this composition feature the drug sucralfate as the common active ingredient. In addition to sucralfate, in Example 6 aspirin has been incorporated; and in Example 7, ibuprofen has been incorporated.

Each composition was formed by first mixing the drugs with a processing aid (glycerin) by mortar and pestle. The excipient, corn syrup solid (Maltrin-365), was slowly added and mixed well. The entire admixture was then processed in a Cuisinart until homogeneous.

Both example mixtures were melt-spun with a modified Tornado spinning machine to allow for control of two parameters: temperature of the heating ribbon, and speed (RPM) of the rotating head. The diameter of the head was 5.5 inches.

The Table below indicates the relative weight percents of the melt-spun components as well as the temperature and rotational speed of the spinning head.

| NSAI PLUS SUCRALFATE | | | | |
|---|---|---|---|---|
| Example Temp C. | Drug wt % | CSS DE = 36.5 wt % | Aid wt % | RPM |
| 6 135 | Sucralfate 10% Aspirin 10% | Maltrin-365 75% | Glycerin 5% | 3,600 |
| 7 135 | Sucralfate 10% Ibuprofen 10% | Maltrin-365 75% | Glycerin 5% | 3,600 |

Flakes were analyzed for the presence of drugs with a Mattson Galaxy 5020 FTIR against a nitrogen purge background. Samples were compared to the FTIR spectra of the individual ingredients.

2 grams of each flake example were ground in a SPEX Wig L Bug ball mill. 5 mg resulting powder was added to 400 mg crystalline KBr and ground again in SPEX mill. This material was split in two equal portions to provide duplicate samples for analysis. Pellets were formed in a SPECAC press by exerting 10 tons of pressure for 1 minute.

IR spectrographs of the melt-spun material confirm the presence of sucralfate in both examples. Spectrographs also confirm that Aspirin was present in the processed sample of Example 6, while Ibuprofen was present in the processed sample of Example 7.

Thus, the product resulting from both example 6 and 7 provide both preventative and therapeutic effect at the site of delivery.

EXAMPLE 8

This example demonstrates the use of HPMC as a thickener in compositions of the present invention. The following composition was formulated:

| INGREDIENTS | WEIGHT % |
|---|---|
| Sulcralfate | 11 |
| Maltrin 365[1] | 68.5 |
| HPMC[2] | 5.2 |
| Sorbitol | 15 |
| Arlacel[3] | 0.27 |

[1]maltodextrin (corn syrup solids) having a dextrose equivalent of 36.5
[2]hydroxypropylmethyl cellulose
[3]trademark for a product containing glycerol monooleate (89%) and propylene glycol (11%)

The Arlacel and HPMC were premixed separately to produce a uniform blend. The sulcrafate, sorbitol and maltodextrin are also separately mixed and the HPMC/Arlacel premix is then added to the sucralfate premix and the two premixes are blended together. Although these ingredients can be mixed simultaneously with the other ingredients, premixing is preferred. The mixture was then divided into two portions. One portion was left as a simple mixture. The other portion was subjected to the flash flow processing of the present invention to form the solid matrix. The mixture was flash flow processed in a 9" cable heater head with a slit width of 0.025" and processed at temperatures ranging from 122°–132° C. and at speeds of 2160–2640 rpm's. The resultant product is a fine, dry flake. These flakes constitute the inventive solid matrix which has been formed from the solid premixed composition.

EXAMPLE 9

This example is intended to demonstrate the wettability and dispersion characteristics of the present invention as compared to simple admixtures of the identical formulations which have not been subjected to the flash flow melt spun process. Two portions, each weighing 36.6 grams a piece of the processed, i.e melt spun, matrices of Example 8 were placed in separate containers and reconstituted with 120 ml of water. One of the containers was shaken 20 times, while the other container was not. The resultant dispersions and wettability charateristics were observed. In the container which was shaken, a fine uniform dispersion resulted. All of the matrix composition was suspended uniformly, demonstrating substantial wettability of the solid flakes. The container which was not shaken showed similiar results. In each instance, the solid matrix rapidly dispersioned upon contact with water.

Figure 2:

Photographs of the two above-mentioned dispersions can be observed in FIGS. 1 and 2. These containers are labelled in the photographs "Processed-Shaken" and "Processed-Unshaken". It is clear from the photographs that dispersions made from the inventive process have enhanced uniformity and wettability as compared to the unprocessed compositions, i.e. those which were not subjected to the flash flow melt spun process, as clearly depicted in FIGS. 1 and 2 and marked accordingly on the containers.

As seen in FIGS. 1 and 2, the containers marked "Unprocessed-Shaken" and "Unprocessed-Unshaken" did not demonstrate complete dispersion or wettability, as evidenced by the caking of the solid mixture on the glass wall of the container. While some dispersion of the material resulted from those solid particles which were appropriately wetted, complete dispersability did not result. This is largely due to the fact that a simple mixture of the components, even when shaken, does not result in complete dissolution of the carrier and subsequent suspension of the particles. The ability of the carrier to rapidly release and uniformly disperse the medicament is critical for many therapies. Additionally, in compositions designed for anti-ulcer treatment, distribution of non-systematic acting medicaments such as sucralfate must be both uniform, complete and effective in adhering to mucosal tissue. As evidenced by the simple shake test, the inventive matrices resulting from flash flow formed compositions, have significantly enhanced dispersion properties which would be expected to be similiarly evidenced in the stomach. As a result of the uniformity in dispersion and excellent wettability of the inventive matrices, the distribution of the medicament is also uniform and provides enhanced bioavialability to the situs of treatment. Thus, the inventive compositions would be expected to disperse more evenly and completely when ingested and with greater speed and efficiency such that adherence to mucosal tissue would likewise be enhanced.

EXAMPLE 10

This example is intended to demonstrate that conventional mixtures of identical ingredients as those used to make the inventive matrices do not result in acceptable dispersions when compared to those made from the inventive compositions. More specifically, two unprocessed samples of the composition of Example 8, each weighing 36.6 gm were added in separate containers to 120 ml of water. One container was shaken 20 times and the resultant dispersion was observed. The other container was not shaken but water was simply added to reconstitute the dry ingredients. The resulting dispersions are depicted in FIGS. 1 and 2 and are marked "Unprocessed-Shaken" and "Unprocessed-Unshaken". FIGS. 1 and 2 show that the dispersions were incomplete at best, with much of the dry powder caking to the bottom of the bottle and failing to wet or go into appreciable suspension. This effect was even more pronounced in the sample which was unshaken.

EXAMPLE 11

This example demonstrates the use of xanthan gum in the inventive compositions. The following composition was formulated:

| INGREDIENTS | WEIGHT PERCENT |
| --- | --- |
| sucralfate | 11.00 |
| Maltrin 365 | 73.25 |
| sorbitol | 15.00 |
| xanthan gum | 0.75 |

A mixture of sucralfate, sorbitol and maltodextrin was blended in a mixer. Xanthan gum was added to this mixture and further blended until uniformity was achieved. A sample of this mixture was then melt spun in accordance with the teachings of this invention. Melt spinning was performed on a 9" cable heater head with a slit width of 0.025 inches and at a temperature range of 122° to 126° C. A small, fine white flake resulted. This matrix product was labelled "Processed." A second sample of the orginally prepared mixture was also separated out but not processed using flash flow processing techniques. This mixture was labelled "Unprocessed."

Figure 3:
Figure 4:

Two samples of the processed melt spun composition, each weighing 36.6 gm were added to separated containers and reconstituted with 120 ml of water. One container was shaken and the other was allowed to remain still. The resultant dispersions were then observed. As seen in FIGS. 3 and 4, the inventive melt spun compositions exhibited excellent wettability and dispersion properties in both the shaken and unshaken containers.

Separate samples of the simple, unprocessed mixture prepared above, each weighing 36.6 gm were reconstituted with 120 ml of water. The separate containers are exhibited in FIGS. 3 and 4 and are labelled "Unprocessed-Shaken" and "Unprocessed-Unshaken." As evidenced in FIGS. 3 and 4, the simple mixtures of the identical ingredients used in the inventive matrices, did not exhibit wettability sufficient to make a uniform or complete dispersion. This is apparent from the caking of the solid powder at the bottom of the containers. This is readily evident in both the shaken and unshaken modes, as seen in the photographs.

It is clear from the above examples that dispersions made from the inventive matrices have better dissolution properties, dispersion properties and wettability characteristics as compared to the same ingredients prepared in simple and conventional mixing procedures. This difference is attributed to the nature and properties of matrices formed from the inventive melt spin process and which allow for enhanced rapid and uniform delivery of medicaments.

The dispersions made in Examples 8 through 11, all exhibited significant stability over several weeks at ambient temperatures. By stability is meant, the suspension of the medicament in the aqueous solutions remained stable without settling out to any significant degree and which can be easily resuspended by moderate shaking, if necessary.

While there have been described what are presently believed to be the preferred embodiments of the invention, those skilled in the art will realize the changes and modifications may be made thereto without departing from the spirit of the invention, and it is intended to claim all such changes and modifications as fall within the true scope of the invention.

What is claimed is:

1. A method of treating mucosal tissue comprising contacting mucosal tissue with a pharmaceutical composition having rapid delivery and enhanced adherence to mucosal tissue, said composition comprising:

a solid matrix having suspended therein a medicament, said matrix formed by flash-flow melt-spinning a mixture comprising i) a melt-spinnable carrier comprising a saccharide present in an amount sufficient to form a flash-flow melt-spun matrix when said medicament is dispersed therein;

ii) a medicament present in an amount sufficient to achieve a therapeutic effect; and iii) a hydrogel selected from the group consisting of gums, alginates, celluloses, pectins, gelatin, polycarbophil and mixtures thereof in an amount sufficient to provide mucosal adherence.

2. The method of claim 1, wherein said carrier material is selected from the group consisting of maltodextrins, corn syrup solids, polydextrose, maltooligosaccharides and mixtures thereof.

3. The method of claim 2, wherein said hydrogel is selected from the group con sist ing of xanthan gum, guar gum, carrageenan gum, gum tragacanth, sodium alginate, gum kayara, locust bean gum, gum acacia and mixtures thereof.

4. The method of claim 3, wherein said hydrogel is present in an amount of from about 0.2 to about 4% by weight of said matrix.

5. The method of claim 1, wherein said hydrogel is hydroxypropylmethylcellulose (HPMC).

6. The method of claim 5, wherein said mixture further comprises an oleaginous substance in an amount sufficient to provide even distribution of said medicament.

7. A method of preparing a pharmaceutical composition having a medicament dispersed in a soluble matrix comprising:

subjecting a feedstock comprising said medicament, a hydrogel selected from the group consisting of gums, celluloses, pectins, gelatin, polvcarbophil, sodium alginate and mixtures thereof and a carrier material to flash-flow transformation.

8. The method of claim 7 wherein said medicament is a drug which acts systematically.

9. The method of claim 8 wherein said drug is selected from the group consisting of anti-infectives and anti-lipid agents.

10. The method of claim 7 wherein said carrier is selected from the group consisting of maltodextrins, corn syrup solids, polydextroses, maltooligo-saccharides and mixtures thereof.

11. The method of claim 7, wherein said hydrogel is selected from the group consisting of xanthan gum, guar gum, carrageenan gum, gum tragacanth, sodium alginate, gum karaya, locus bean gum, gum acacia and mixtures thereof.

12. The method of claim 11 wherein said hydrogel is present in an amount of from about 0.2 to about 4% by weight of said matrix.

13. The method of claim 7 wherein said matrix further contains an oleaginous substance in an amount sufficient to provide even distribution of said medicament.

14. The method of claim 13 wherein said oleaginous substance is selected from the group consisting of corn oil, sunflower oil, olive oil, vegetable oils and mixtures thereof.

15. The method of claim 7 wherein said hydrogel is selected from the group consisting of hydroxypropylmethylcellulose, hydroxyethylcellulose, methylcellulose, carboxymethylcellulose, hydroxymethylcellulose and mixtures thereof.

16. A method for increasing efficacy of a medicament by enhancing the adherence and the speed of contact of said medicament to mucosal tissue comprising administering a medicament suspended in a solid matrix, said matrix formed by flash-flow melt-spinning:

i) a carrier comprising a saccharide in an amount sufficient to form a melt-spun matrix when a medicament is dispersed therein;

ii) a medicament present in an amount sufficient to achieve a therapeutic effect; and iii) a hydrogel selected from the group consisting of gums, celluloses, pectins, gelatin, polycarbophil, sodium alginate and mixtures thereof in an amount sufficient to provide mucosal adherence.

* * * * *

UNITED STATES PATENT AND TRADEMARK OFFICE
CERTIFICATE OF CORRRECTION

PATENT NO. : 5,811,123
DATED      : September 22, 1998
INVENTOR(S) : Fuisz It is certified that error appears in the above-identified patent and that said Letters Patent is hereby corrected as shown below:

On the title page: Item [56] insert the following:

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 5 | 4 | 6 | 4 | 6 | 3 | 2 | 11/1995 | Cousin et al | | | |
| | | | | | | | | | | | | | |

Signed and Sealed this

Twenty-seventh Day of April, 1999

Attest:

Q. TODD DICKINSON

*Attesting Officer*   *Acting Commissioner of Patents and Trademarks*